(12) United States Patent
Burn

(10) Patent No.: US 8,540,680 B2
(45) Date of Patent: Sep. 24, 2013

(54) MEDICAL LINE SECUREMENT DEVICE WITH LOCATING GUIDES

(75) Inventor: Brian M. Burn, Lawrenceville, GA (US)

(73) Assignee: C.R. Bard, Inc., Covington, GA (US)

( * ) Notice: Subject to any disclaimer, the term of this patent is extended or adjusted under 35 U.S.C. 154(b) by 771 days.

(21) Appl. No.: 12/175,365

(22) Filed: Jul. 17, 2008

(65) Prior Publication Data
US 2009/0143741 A1    Jun. 4, 2009

Related U.S. Application Data

(60) Provisional application No. 60/950,231, filed on Jul. 17, 2007.

(51) Int. Cl.
*A61M 5/32* (2006.01)

(52) U.S. Cl.
USPC .................. 604/177; 604/174; 604/180

(58) Field of Classification Search
USPC .................................. 604/174–180
See application file for complete search history.

(56) References Cited

U.S. PATENT DOCUMENTS

| | | |
|---|---|---|
| 2,525,398 A | 10/1950 | Collins |
| 2,533,961 A | 12/1950 | Rousseau et al. |
| 2,707,953 A | 5/1955 | Ryan |
| 3,059,645 A | 10/1962 | Hasbrouck et al. |
| 3,064,648 A | 11/1962 | Bujan |
| 3,167,072 A | 1/1965 | Stone et al. |
| 3,568,679 A | 3/1971 | Reif |
| 3,574,306 A | 4/1971 | Alden |
| 3,602,227 A | 8/1971 | Andrew |
| 3,677,250 A | 7/1972 | Thomas |
| 3,766,915 A | 10/1973 | Rychlik |
| 3,856,020 A | 12/1974 | Kovac |
| 3,900,026 A | 8/1975 | Wagner |
| 3,906,946 A | 9/1975 | Nordström |
| 3,920,001 A | 11/1975 | Edwards |
| 3,942,228 A | 3/1976 | Buckman et al. |
| 3,973,565 A | 8/1976 | Steer |
| 4,020,835 A | 5/1977 | Nordstrom et al. |
| 4,025,015 A | 5/1977 | Kolic |
| 4,059,105 A | 11/1977 | Cutruzzula et al. |
| 4,082,094 A | 4/1978 | Dailey |
| 4,116,196 A | 9/1978 | Kaplan et al. |
| 4,129,128 A | 12/1978 | McFarlane |
| 4,161,177 A | 7/1979 | Fuchs |
| 4,250,880 A | 2/1981 | Gordon |
| 4,316,461 A | 2/1982 | Marais et al. |

(Continued)

FOREIGN PATENT DOCUMENTS

| | | |
|---|---|---|
| DE | 2341 297 A1 | 8/1973 |
| EP | 0 169 704 | 1/1986 |

(Continued)

*Primary Examiner* — Kevin C Sirmons
*Assistant Examiner* — Imani Hayman
(74) *Attorney, Agent, or Firm* — Knobbe, Martens, Olson & Bear, LLP

(57) ABSTRACT

An anchoring system includes a securement device having an anchor pad with a flexible retainer opening that receives a portion of a medical article, such as a catheter, to hold it securely in place. A locating mechanism in the form of posts positions and holds the catheter in position and limits rotational movement of the catheter. The anchor pad is secured to a patient's skin by adhesive.

30 Claims, 9 Drawing Sheets

(56) References Cited

U.S. PATENT DOCUMENTS

| | | |
|---|---|---|
| 4,326,519 A | 4/1982 | D'Alo et al. |
| 4,397,647 A | 8/1983 | Gordon |
| 4,405,163 A | 9/1983 | Voges et al. |
| 4,453,933 A | 6/1984 | Speaker |
| 4,480,639 A | 11/1984 | Peterson et al. |
| 4,633,863 A | 1/1987 | Filips et al. |
| 4,660,555 A | 4/1987 | Payton |
| 4,711,636 A | 12/1987 | Bierman |
| 4,742,824 A | 5/1988 | Payton et al. |
| 4,752,292 A | 6/1988 | Lopez et al. |
| 4,795,429 A | 1/1989 | Feldstein |
| 4,826,486 A | 5/1989 | Palsrok et al. |
| D301,684 S | 6/1989 | Herzog |
| 4,852,844 A | 8/1989 | Villaveces |
| 4,857,058 A | 8/1989 | Payton |
| 4,880,412 A | 11/1989 | Weiss |
| 4,897,082 A | 1/1990 | Erskine |
| 4,898,587 A | 2/1990 | Mera |
| 4,919,654 A | 4/1990 | Kalt |
| 4,955,864 A | 9/1990 | Hajduch |
| 4,997,421 A | 3/1991 | Palsrok et al. |
| 5,084,026 A | 1/1992 | Shapiro |
| 5,090,645 A | 2/1992 | Zuercher |
| 5,137,519 A | 8/1992 | Littrell et al. |
| 5,192,273 A | 3/1993 | Bierman et al. |
| 5,192,274 A | 3/1993 | Bierman |
| 5,209,441 A | 5/1993 | Satoh |
| 5,354,282 A | 10/1994 | Bierman |
| 5,382,239 A | 1/1995 | Orr et al. |
| 5,413,562 A | 5/1995 | Swauger |
| 5,415,287 A | 5/1995 | Hamano et al. |
| 5,456,671 A | 10/1995 | Bierman |
| 5,470,321 A | 11/1995 | Forster et al. |
| 5,484,425 A | 1/1996 | Fischell et al. |
| 5,496,282 A | 3/1996 | Militzer et al. |
| 5,496,283 A | 3/1996 | Alexander |
| 5,578,013 A | 11/1996 | Bierman |
| 5,693,032 A | 12/1997 | Bierman |
| 5,702,369 A | 12/1997 | Mercereau |
| 5,702,371 A | 12/1997 | Bierman |
| D389,911 S | 1/1998 | Bierman |
| 5,722,959 A | 3/1998 | Bierman |
| 5,810,781 A | 9/1998 | Bierman |
| D399,954 S | 10/1998 | Bierman |
| 6,032,433 A | 3/2000 | Hatziathanasiou |
| 6,213,979 B1 | 4/2001 | Bierman |
| 6,224,571 B1 | 5/2001 | Bierman |
| 6,491,664 B2 | 12/2002 | Bierman |
| 6,582,403 B1 | 6/2003 | Bierman et al. |
| 6,929,625 B2 | 8/2005 | Bierman |
| 6,979,320 B2 | 12/2005 | Bierman |
| 7,223,256 B2 | 5/2007 | Bierman |
| 7,722,571 B2 | 5/2010 | Bierman et al. |
| 7,981,087 B2 | 7/2011 | Gesler |
| 2007/0078400 A1* | 4/2007 | Gesler, III ................ 604/177 |
| 2007/0173766 A1* | 7/2007 | Bierman ................... 604/174 |
| 2010/0100051 A1* | 4/2010 | Bierman ................... 604/180 |

FOREIGN PATENT DOCUMENTS

| | | |
|---|---|---|
| EP | 0 690 704 A1 | 1/1986 |
| EP | 0 247 590 A2 | 12/1987 |
| GB | 2 063 679 A | 6/1981 |
| GB | 2 086 466 A | 5/1982 |
| WO | WO 80/01458 | 7/1980 |
| WO | WO 92/19309 | 11/1992 |
| WO | WO 98/53872 | 12/1998 |

* cited by examiner

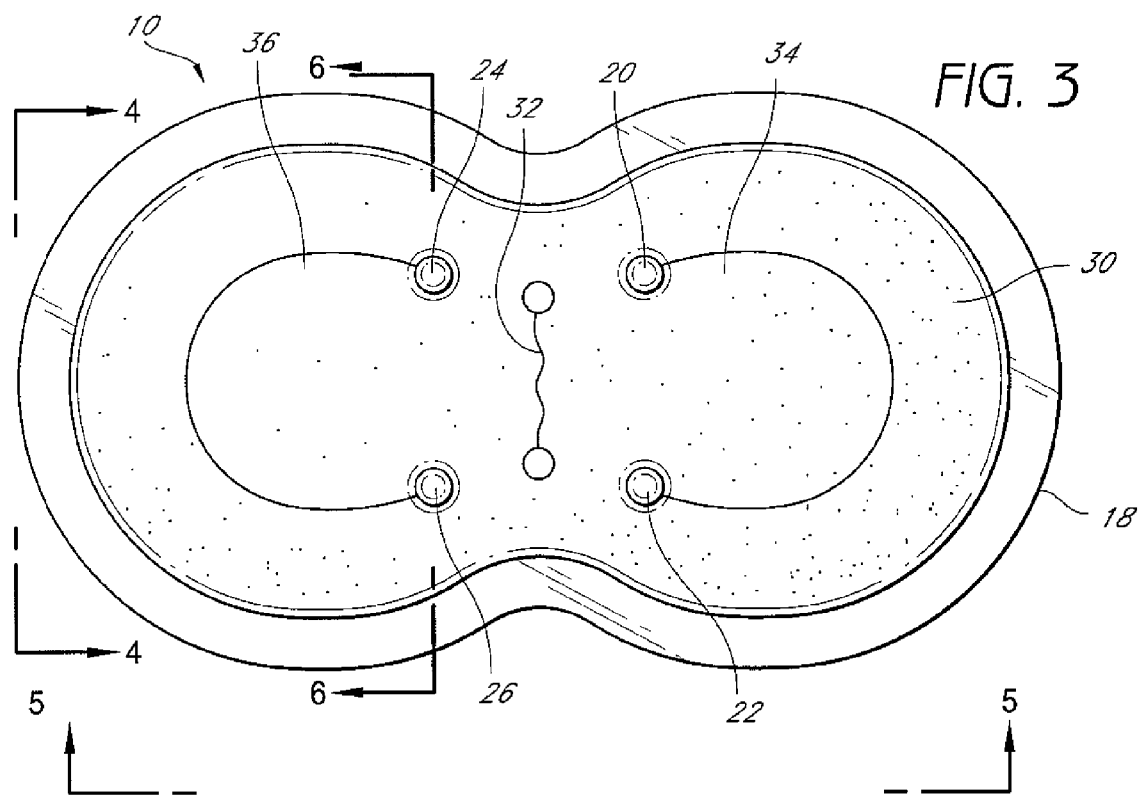
FIG. 3
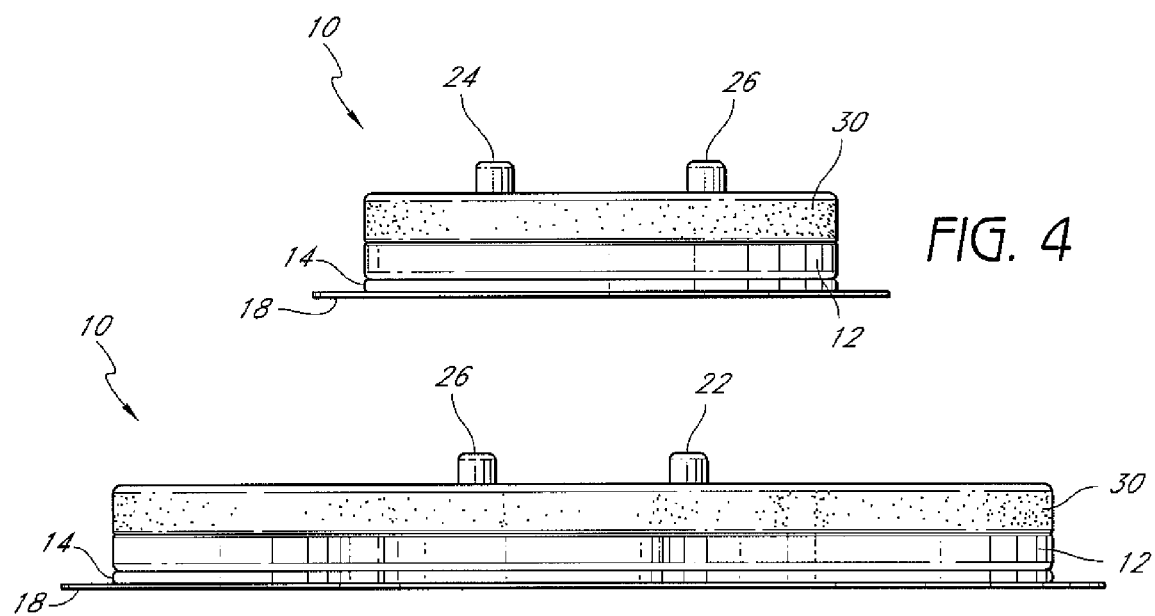
FIG. 4
FIG. 5
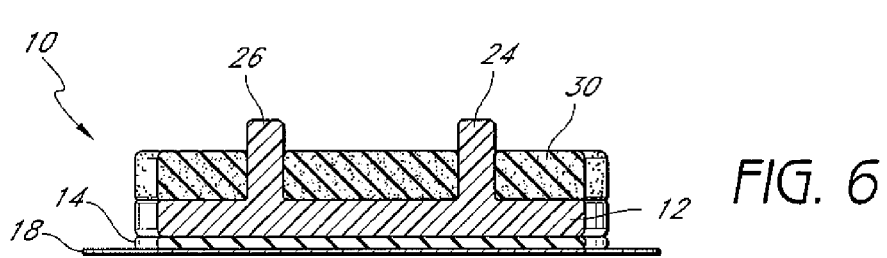
FIG. 6

MEDICAL LINE SECUREMENT DEVICE WITH LOCATING GUIDES

CROSS-REFERENCE TO RELATED APPLICATION

This application claims the benefit of U.S. Provisional Application No. 60/950,231, filed on Jul. 17, 2007, which is incorporated herein by reference in its entirety.

BACKGROUND OF THE INVENTION

1. Field of the Invention

This invention relates to an anchoring system for securing a medical article to a patient and, in particular, to an anchoring system for securing a catheter or other elongated medical article to a patient to inhibit movement or migration of the catheter or medical article relative to the patient.

2. Description of the Related Art

It is common in the treatment of patients to utilize catheters to introduce fluids and medications directly into the patient or to withdraw fluids from the patient. Percutaneously inserted catheters direct fluids directly into the bloodstream, a specific organ or an internal location within the patient, or are used to monitor vital functions of the patient. For instance, short, peripherally-inserted, intra-arteriovenous catheters are commonly used to direct fluids and/or medications directly into the bloodstream of the patient. The fluid (e.g., parenteral liquid, medication, etc.) typically drains from a container positioned above the patient to feed under gravity or is delivered via an infusion pump. The fluid flows through tubing and into the indwelling catheter. The catheter and the fluid tubing are commonly removably attached to each other by a conventional luer-lock connector.

In many cases, the catheter remains in place for several days or weeks. In order to secure the catheter in position at the insertion site, a health care provider often secures the catheter to the patient using tape, adhesive, or foam. In one common type of application, the health care provider places long pieces of tape across a section of the catheter near the insertion site in a crisscross pattern to secure the catheter to the patient's skin. The health care provider wraps a thin piece of tape around the hub of the catheter and then forms a "chevron" with the tape, placing the ends next to the sides of the indwelling catheter. Then, one piece of tape is placed across and over the catheter hub, to form a loop in the tubing. Another piece of tape is placed across the tubing loop, and an additional piece of tape is placed over the catheter hub and the tubing section that has been looped around to extend next to the indwelling catheter. Subsequently, the health care provider typically covers the insertion site and the indwelling catheter with a transparent dressing. This securement inhibits movement of the catheter relative to the insertion site, as well as prevents the catheter from snagging on the bed rail or other objects.

Tape, however, often collects dirt and other contaminates. Normal protocol therefore requires periodic (e.g., daily) tape changes to inhibit bacteria and germ growth at the securement site. Frequent tape changes, however, create the problem of excoriation of the patient's skin. Additionally, valuable time is spent applying and reapplying the tape. Further, because many health care providers find the taping procedure difficult and cumbersome when wearing latex gloves, they often remove their gloves when taping. Not only does this further lengthen the taping procedure, but it also subjects the health care provider to possible infection. Moreover, even if health care providers remain gloved, contact between the adhesive surface of the tape and the latex gloves causes micro-holes in the gloves, which also subjects the health care provider to possible infection.

The entire taping and dressing procedure takes several minutes of the health care provider's valuable time. In addition, the catheterization process often requires relatively frequent disconnection between the catheter and the fluid supply tube, as well as dressing changes. For instance, intravenous catheterization is frequently maintained for several days, depending upon the condition of the patient. The tubing is generally replaced every 48 to 72 hours in order to maintain the sterility of the fluid and the free-flow of the fluid through the tubing. A health care provider thus must frequently change the tubing and re-tape the connection. The health care provider also must frequently clean the insertion site about the indwelling catheter and change the dressings.

In addition, the traditional method of intravenous catheter securement with surgical tape and transparent dressings alone has not always prevented catheter migration and/or dislodgment. Taped intravenous catheters are easily pulled out during a "routine" dressing change, especially by inexperienced health care providers. Further, if the catheter migrates too far or dislodgment occurs, the health care provider must replace the catheter, thus exacerbating the time and expense required to maintain the intravenous feed.

Prior securement methods also have not served the patient well. Surgical tape or foam strips are uncomfortable. Many patients also do not rest comfortably and worry about catheter dislodgment when they move, when only tape and a dressing secure the catheter in place.

As an alternative to tape securement, some catheters include an integrated or a movable flexible clamp with winged extensions. These extensions are sutured to the patient's skin in order to secure the catheter in position at the insertion site. In other applications, the flexible clamp is covered by a rigid box clamp, which receives the catheter/clamp combination in a friction-fit manner. The rigid box clamp and the flexible clamp have lateral, aligned holes in them, which allow the combination to be sutured to the patient's skin. Although this technique securely attaches the catheter to the patient, it obviously is painful and uncomfortable for the patient. This prior retention procedure is also time consuming and inconvenient, poses the risk of needle-stick to the health care provider, and risks suture-site infection to the patient.

Suture material also tends to exhibit poor gripping on medical tubes and can cut through the winged extension of the flexible clamp, if a rigid clamp is not used. The use of a rigid clamp, however, complicates the securement procedure by adding yet another component that can be dropped on the floor and become unsterile. In addition, the sutured securement of the flexible clamp or the flexible/rigid clamp assembly does not permit easy release of the catheter from the patient for dressing changes and insertion site cleansing.

A number of catheterization systems have been developed to improve the stability of the catheter and to obviate the need for frequent application and removal of surgical tape. Prior devices, however, have generally held the connector on the IV tubing securely against the patient, rather than the catheter fitting itself.

There is a need for a device that can safely and securely retain a medical article, such as a catheter, to a patient while allowing the medical article to be released and retained without disturbing the patient. There is also a need for a device that can assist medical personnel in properly positioning a medical article with respect to a retainer and to hold the medical article in the originally mounted position in a secure manner.

SUMMARY

One aspect of the invention is directed to a securement device for securing a medical article to a patient. The device includes an adhesive layer configured to contact a patient's skin, a base, and an anchor pad supported by the base. The anchor pad includes an opening and a flexible tab. The opening is configured to receive a portion of the medical article. The flexible tab covers at least a portion of the base and is movable with respect to the base between a first position in which a cavity between the base and the anchor pad is at least partially exposed to receive at least a portion of the medical article and a second position in which at least a portion of the anchor pad covers at least a portion of the received medical article. The device further includes locating protrusions extending at least partially between the base and the anchor pad at least when the flexible tab is in the second position and the received portion of the medical article is disposed within the cavity. The protrusions define at least in part a mounting position in the cavity for the received portion of the medical article.

Another aspect is directed to a securement device for positioning a catheter on a patient. The device comprises a base that has an adhesive bottom surface and a top surface with locating formations protruding therefrom. The device further includes a flexible anchor pad disposed on the base that defines a cavity between a portion of the base and a portion of the anchor pad. The anchor pad includes an elongated opening to the cavity. The locating formations at least partially define the cavity and limit movement of the catheter in at least one direction.

Another aspect is directed to a method of securing a medical article to a Patient's skin. The method includes adhering an anchor pad with a base onto a patient's skin and deforming a tab on the anchor pad to provide access to a cavity formed between the anchor pad and the base via an opening. The method further includes inserting a portion of the medical article into the cavity and abutting at least a portion of the medical article against at least one formation that partially defines the cavity. The method further includes locating at least a portion of the medical article in the opening and releasing the tab so as to inhibit access to the cavity via the opening.

Another aspect is directed to an anchoring system for securing a medical line to the body of a patient. The system includes a fitting on a medical line and a retainer that has a lower layer that defines a receiving area for receiving a portion of the fitting, an upper layer, and first and second pairs of posts. At least a portion of the upper layer is movable between a closed position in which at least a portion of the upper layer extends over at least a portion of the receiving area and an open position in which the receiving area is at least partially open. The first and second pairs of posts extend between the lower layer and the upper layer at least when the upper layer is in the closed position. At least two of the posts of the first and second pairs of posts are disposed on the receiving area and spaced apart so as to receive at least a first portion of the fitting therebetween. At least two other posts of the first and second pairs of posts are disposed on the receiving area and spaced apart so as to receive at least a second portion of the fitting therebetween. At least a portion of each of the first and second pairs of posts is located at least partially beneath the upper layer when the upper layer is in the closed position.

Another aspect is directed to an anchoring system for securing a medical article to the body of a patient. The system includes a retainer that has a lower layer that defines a receiving area for receiving a portion of the medical article, an upper layer, a first post support and a second post support. At least a portion of the upper layer is flexible so as to move between a closed position in which at least a portion of the upper layer extends over at least a portion of the receiving area and an open position in which the receiving area is at least partially open. The first and second post supports extend across at least a portion of the receiving area and between the lower layer and the upper layer. The first post support is disposed on a side of the receiving area. The second post support is disposed on the other side of the receiving area and spaced from the first post support so as to receive at least a portion of the medical article therebetween.

Another aspect is directed to a securement device for securing a medical line to a body of a patient. The medical line has a fitting that includes a pair of laterally extending wings. The device includes a base layer that has a mounting surface at least partially covered by an adhesive for attaching the securement device to the body of the patient, and a receiving surface accessible from an opposite side of the base layer. The device further includes a retainer layer disposed on the base layer and having a peripheral edge, and at least one interior wall formed by the retainer layer, the interior wall extending generally normal to the receiving surface and being disposed within the peripheral edge of the retainer layer, the interior wall and the receiving surface of the base layer together defining at least a portion of a space at least when the fitting is retained by the securement device, the space being configured to receive at least a portion of one of the laterally extending wings of the fitting. The device further includes at least one protrusion extending from the base layer adjacent to the space and configured to abut against at least a portion of the received lateral wing.

Another aspect is directed to a securement device for securing a fitting on a medical line that has an elongated body to a body of a patient. The fitting includes at least one laterally extending surface that projects beyond the body of the medical line from at least one side of the medical line. The securement device a lower layer that has a mounting surface at least partially covered by an adhesive layer for attaching the securement device to the patient's body and a receiving surface oriented so as to face away from the patient's body, the receiving surface including at least two posts spaced apart so as to receive at least a portion of the at least one laterally extending surface of the fitting therebetween, an upper layer disposed on the lower layer and defining a receiving space at least when the fitting is retained by the securement device, at least a portion of the upper layer including a flexible tab, the flexible tab being movable so as to expose at least a portion of the receiving surface between the lower layer and the upper layer for receiving the laterally extending surface of the fitting.

Another aspect is directed to a method of securing a fitting that includes a first lateral wing and a second lateral wing to a body of a patient. The method includes adhering a securement device to the skin of a patient, the securement device comprising a base layer and at least one post, the base layer supporting a first deflectable structure and a second deflectable structure, at least a portion of each deflectable structure being arranged generally parallel to the base layer so as to define a receiving space therebetween at least when the fitting is retained by the securement device, the at least one post being disposed relative to the receiving space so as to locate at least a portion of the fitting on the receiving space, moving the first deflectable structure in a first direction away from a central point between the receiving spaces, moving the second deflectable structure opposite to the first direction away from the central point, inserting at least a portion of the first lateral wing in the corresponding receiving space and adjacent to the at least one post, releasing the first deflectable structure to partially cover the first lateral wing, inserting at least a portion of the second lateral wing in the corresponding receiving space, and releasing the second deflectable structure to partially cover the second lateral wing.

Another aspect is directed to a securement device for securing a medical article to a patient comprising a base having an adhesive bottom surface and a top surface and an anchor pad disposed on the top surface of the base. The anchor pad includes a retainer opening formed therein configured to receive a portion of the medical device and a flexible tab that covers a portion of the base and can be lifted to expose a cavity between the anchor pad and the top surface of the base configured to receive a portion of the medical article. Locating protrusions extend from the base adjacent to the tab that define a mounting position in the cavity for the portion of the medical article.

Another aspect is directed to a securement device for positioning a catheter on a patient comprising a base having an adhesive bottom surface and a top surface with locating formations and a flexible anchor pad disposed on the base and defining a cavity between a portion of the base and a portion of the anchor pad. The anchor pad includes an elongated retainer opening to the cavity, wherein the locating formations define a channel to receive a portion of the catheter in the cavity and limit rotation of the catheter within the cavity.

Another aspect is directed to a method of securing a medical article to a Patient's skin comprising determining placement of the medical article on the patient, adhering an anchor pad with a base onto the patient's skin, deforming a tab on the anchor pad to open a retaining formation in the anchor pad and provide access to a cavity between the anchor pad and the base, inserting a portion of the medical article into the cavity, positioning the portion of the medical article within the cavity using locator formations extending from the base, and releasing the tab so to close the retaining formation against the medical article and thereby couple the medical article to the anchor pad.

These and other aspects of the invention will become apparent when taken in conjunction with the detailed description and appended drawings.

BRIEF DESCRIPTION OF THE DRAWINGS

The above-mentioned and other aspects of the invention will now be described in conjunction with the accompanying drawings in which like reference numerals indicate corresponding parts in the different figures.

FIG. 3 is a top view of the securement device of FIG. 2.
FIG. 4 is a side view of the securement device of FIG. 2.
FIG. 5 is a front view of the securement device of FIG. 2.
FIG. 6 is a cross-sectional view of the securement device of FIG. 2 showing protrusions extending through the anchor pad.

DETAILED DESCRIPTION OF THE PREFERRED EMBODIMENTS

This invention is directed to an anchoring system for a medical article and is disclosed in the context of an exemplary intravenous (IV) catheter. The principles of the present invention, however, are not limited to IV catheters. Instead, it will be understood by one of skill in this art, in light of the present disclosure, that the anchoring system and retainer disclosed herein also can be successfully utilized in connection with other types of medical articles, including other types of catheters, fluid drainage and delivery tubes and electrical wires. For example, but without limitation, the retainer disclosed herein can also be configured to receive and secure central venous catheters (CVC), peripheral catheters, peripherally inserted central catheters (PICC), Foley catheters, hemodialysis catheters, surgical drainage tubes, feeding tubes, chest tubes, nasogastric tubes, scopes, as well as electrical wires or cables connected to external or implanted electronic devices or sensors. Many of these devices include either an integrated or movable fitting (e.g., a winged fitting) with one or more securement apertures. The catheter in the illustrated embodiment includes a winged fitting, but it is not necessary for this invention, as the positioning mechanism can be used with any portion of a medical line. One skilled in the art may also find additional applications for the devices and systems disclosed herein. Thus, the illustration and description of the anchoring system in connection with a catheter is merely exemplary of one possible application of the anchoring system.

According to various embodiments, the device disclosed herein is an improvement of the WingGuard® PICC securement device sold by Tri-State Hospital Supply Corporation, Howell, Mich.

Figure 2:
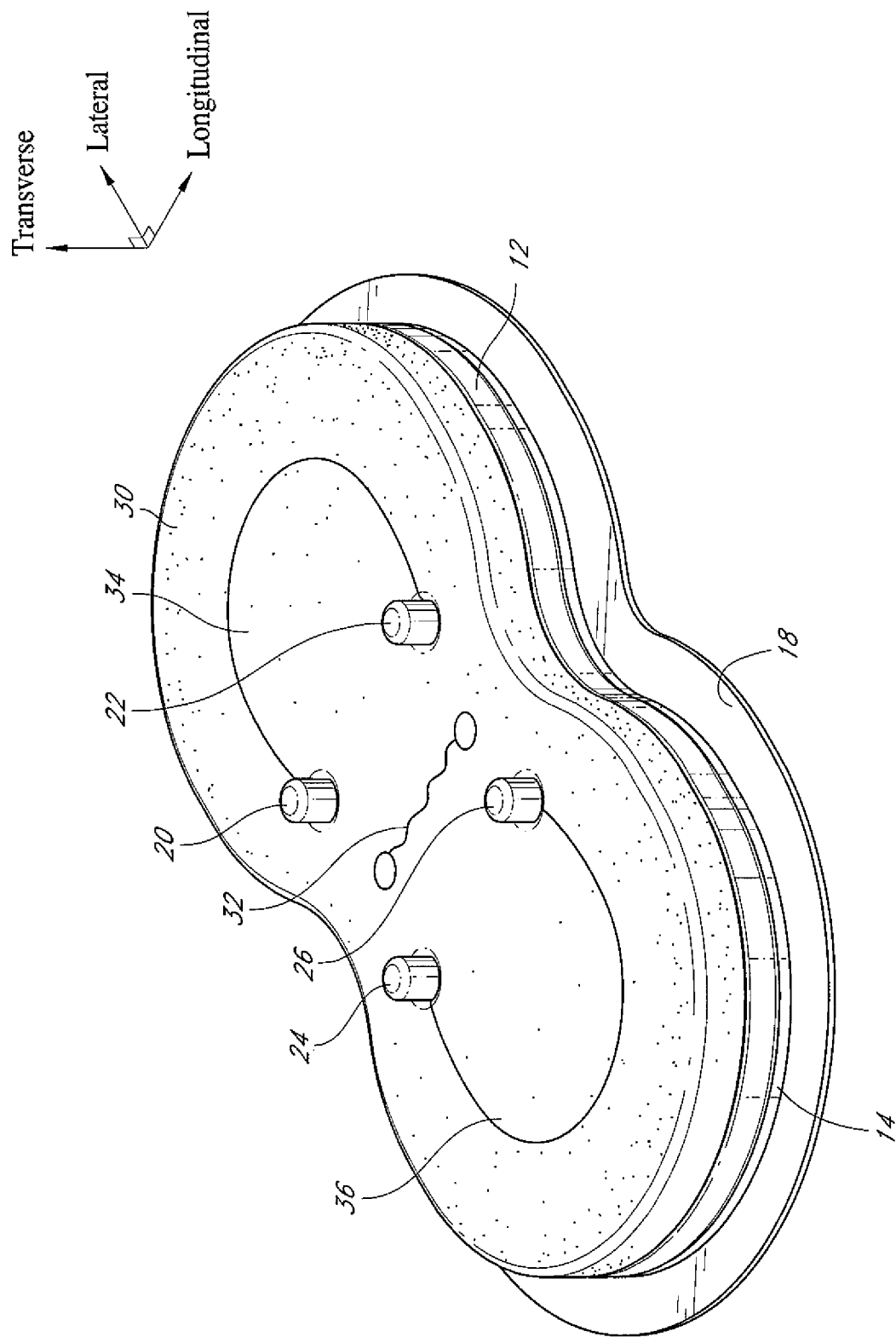
FIG. 2 is a perspective view of the securement device from FIG. 1.

To assist in the description of these components of the securement device, the following coordinate terms are used. A "longitudinal axis" is generally parallel to the major axis of the medical line or article (further described below). A "lateral axis" is normal to the longitudinal axis and is generally parallel to the plane of a base 12, as seen in FIG. 2. A "transverse axis" extends normal to both the longitudinal and lateral axes. In addition, as used herein, "the longitudinal direction" refers to a direction substantially parallel to the longitudinal axis; "the lateral direction" refers to a direction substantially parallel to the lateral axis; and "the transverse direction" refers to a direction substantially parallel to the transverse axis. The terms "upper," "lower," "top," "bottom," and the like, which also are used to describe the present support device, are used in reference to the illustrated orientation of the embodiment. A detailed description of a preferred embodiment of the support device, and its associated method of use, now follows.

Figure 1:
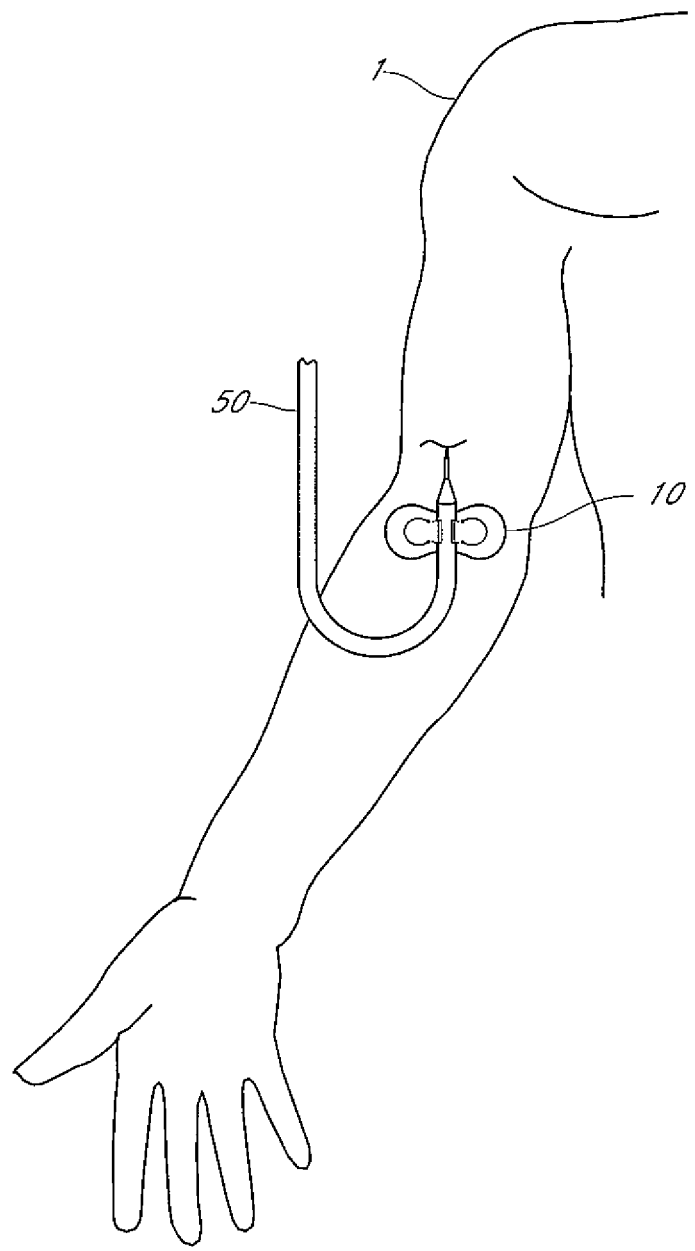
FIG. 1 is a diagram of a medical article secured to a patient with a securement device in accordance with a preferred embodiment of the present invention.

FIG. 1 is a diagram of a medical article 50 secured to a patient 1 with a securement device 10. A characteristic of certain embodiments of the anchoring system is releasable engagement of the medical article 50 to the patient 1. The securement device 10 allows the medical article 50, such as a catheter, to be disconnected from the securement device 10, and from the patient 1, for any of a variety of known purposes. For instance, the health care provider may want to remove the catheter from the securement device 10 to ease disconnection of the catheter from the insertion point or to clean the patient. The disengagement of the catheter from the securement device 10, however, can be accomplished without removing the securement device 10 from the patient 1. In addition, the disengagement can be accomplished without destroying the securement device 10 and without the use of tools, such as, for example, a hemostat or surgical clamp.

The securement device inhibits movement of the secured medical article 50 relative to the patient in at least direction. For example, the securement device may inhibit lateral, transverse, and rotational movement of the catheter with respect to the securement device 10. In certain embodiments, the securement device 50 inhibits longitudinal motion in one or both longitudinal directions. Rotational movement about the transverse axis is generally inhibited by the holding effect provided by the formations, guides, or posts. In combination, the formations, guides, or posts, the retaining mechanism, and the anchor pad and base may inhibit movement of the catheter which could otherwise cause the catheter fitting to rock, roll, slip, or slide, as is described further below.

FIG. 2 is a perspective view of a securement device according to one embodiment of the invention. The device 10 includes a base or lower layer 12, an anchor pad or upper layer 30, and one or more guides, posts, or locating formations 20, 22, 24, 26. A cavity or space 38 is formed between at least a portion of the base 12 and at least a portion of the anchor pad 30.

The device 10 may further include an adhesive surface or layer 14 configured to adhere to a patient's skin. The adhesive 14 can be biocompatible and applied with known methods, including transfer tape and sputtering. The adhesive 14 may be a medical-grade adhesive layer that can be either diaphoretic or nondiaphoretic, depending on the particular application. A release sheet 18 can be disposed over the adhesive surface 14 for removal upon application to a patient's skin. In some embodiments, the release sheet 18 resists tearing and is divided into a plurality of pieces to assist in attachment to a patient. The sheet 18 can be split along its center line so that only half of the adhesive surface 14 is exposed at a time. It can extend beyond, for example, at least one edge of the base 12 to facilitate removal of the sheet from the adhesive surface 14. Any known material can be used as the sheet 18. For example, one suitable material is polycoated, siliconized paper. In other embodiments, multiple securement devices are attached via the adhesive 14 to a single release sheet 18. The release sheet 18 may be perforated such that individual securement devices may be easily obtained without removing the release sheet 18 from the adhesive surface 14.

The adhesive surface or layer 14 may be disposed on a portion of the base 12 or on a separate layer from the base 12 and the anchor pad 30. For example, the separate layer may have a bottom adhesive surface for contacting the patient and a top surface attached to a bottom surface of the base 12.

The base 12 is preferably flexible and forms a structural layer which supports the anchor pad 30. The base 12 can be formed of any suitable material, such as plastics, including, but not limited to, polypropylene or polyethylene. One suitable exemplary material is low density polyethylene (LDPE) commercially available as Tenite® from Eastman Chemical Company. One form of construction includes injection molding.

The one or more locating formations 20, 22, 24, and 26 are disposed so as to extend from the base 12, anchor pad 30 and/or both the base 12 and anchor pad 30 and across at least a portion of the cavity 38 when the medical article is secured within the cavity 38. In certain embodiments, each formation 20, 22, 24, 26 includes first portions and corresponding second portions. The first portion can extend from the base 12 while the corresponding second portion extends from the anchor pad 30 towards the first portion. Together, the first and second portions form one formation. In the illustrated embodiment, the formations 20, 22, 24, 26 extend from the base 12.

The portion(s) of the formations 20, 22, 24, and 26 that extend across or traverse all or a portion of the cavity 38 define one or more abutment surfaces. The abutment surfaces are configured to contact the secured medical article so as to inhibit movement of the medical article in at least one direction. Of course the medical article need not contact each abutment surface when secured in the device 10.

The formations 20, 22, 24, and 26 may have different lengths and sizes. The formations 20, 22, 24, and 26 may extend across the entire cavity 38 or just a portion of the cavity 38. Preferably, the formations 20, 22, 24, and 26 extend across a sufficient portion of the cavity 38 in a generally transverse direction at least when the medical article is secured within the cavity 38 so as to inhibit rotation of the medical article about the transverse axis.

The formations 20, 22, 24, and 26 may further extend through corresponding openings or receptacles in the anchor pad 30 or base 12 depending on from which surface the formations extend. In the illustrated embodiment, the formations 20, 22, 24, and 26 extend from the base 12 and through corresponding openings in the anchor pad 30. The formations 20, 22, 24, and 26 may extend through the anchor pad 30 and above a top surface of the anchor pad 30 when the medical article is, or is not, secured in the cavity 38. The formations 20, 22, 24, and 26 may extend a first distance into or through the anchor pad 30 before the medical article is placed within the cavity 38 and a second distance into or through the anchor pad 30 after the medical article is secured within the cavity 38. For example, the formations 20, 22, 24, and 26 may extend entirely through the anchor pad 30 before the medical article is secured in the device 10. When the medical article is secured and the cavity 38 is formed, the same formations 20, 22, 24, and 26 may extend to a lesser extent through the anchor pad 30 or not at all. Of course the formations 20, 22, 24, and 26 are not limited to the disclosed shapes and sizes.

The locating formations 20, 22, 24, 26 may be formed as protrusions, posts, ridges, guides, or any other structure that provides an abutment surface for inhibiting movement of a secured medical article when placed within the cavity 38 in at least one direction. The formations 20, 22, 24, and 26 may have any shape, but a rounded shape may be advantageous to assist with positioning as explained below. The formations 20, 22, 24, and 26 may be separate structure attached to the base 12 or anchor pad 30 or a unitary structure with the device 10. For example, the base 12 and the locating formations 20, 22, 24, 26 can be formed as an integral element in one piece. This can be accomplished in a variety of known ways, including for example, injection molding. The abutment surfaces on the locating formations 20, 22, 24, 26 may define a portion of a channel, passageway, or groove, as explained below.

In the illustrated embodiment, the anchor pad 30 is disposed on a top surface of the base 12. The anchor pad 30 can be a flexible sheet made of foam, such as closed-cell polyethylene foam. The anchor pad 30 can be made of silicon. An advantage of silicon is that it is highly durable, flexible and allows for dressings and tapes to be cleanly removed from the anchor pad 30. The material should be deformable but sufficiently resilient to return to its original shape. The anchor pad 30 may be designed in any shape or configuration. As seen, the anchor pad 30 and base 12 are formed with a central narrowed portion that provides the peripheral ends with a larger contact area to provide greater stability and adhesion to a patient's skin while the center section that supports the medical article can be placed close to the insertion site.

The anchor pad 30 can be in one or more portions and includes a retainer opening or gap 32 formed therein or between portions. In an embodiment the anchor pad 30 comprises two portions arranged side by side with the retainer opening 32 being formed at the interface between the portions.

In the illustrated embodiment, the anchor pad 30 is formed from a single piece with the retainer opening 32 formed therein. The opening 32 can have any shape. For example, the opening or slit can have straight or irregular edges. The opening 32 is configured to receive a portion of the medical article and provide an entrance to the cavity 38.

The device includes at least one flexible tab 34, 36, The flexible tab 34, 36 is configured so that when pulled the opening 32 and/or cavity 38 expand to facilitate placement of a portion of the medical article in the cavity 38. The flexible tab 34, 36 can be integrally formed with the anchor pad or upper layer 30 or a separate structure attached to the anchor pad 30. The illustrated embodiment includes two flexible tabs 34, 36 integrally formed in the pad 30. For ease of description, the flexible tabs 34, 36 and considered part of the anchor pad 30 but of course need not be to fall within the scope of the invention.

At least a portion of the pad 30 is secured to the base 12 so as to prevent the pad 30 from entirely separating from the base 12 at least when the medical article is secured within the cavity 38. In certain embodiments, the pad 30 is secured to the base 12 at one or more locations around the peripheral edge of the pad 30. Of course the pad 30 need not be secured around its peripheral edge or around its entire periphery to the base 12. In the illustrated embodiment, the flexible tabs 34, 36 are not secured directly to the base 12.

Figure 8:
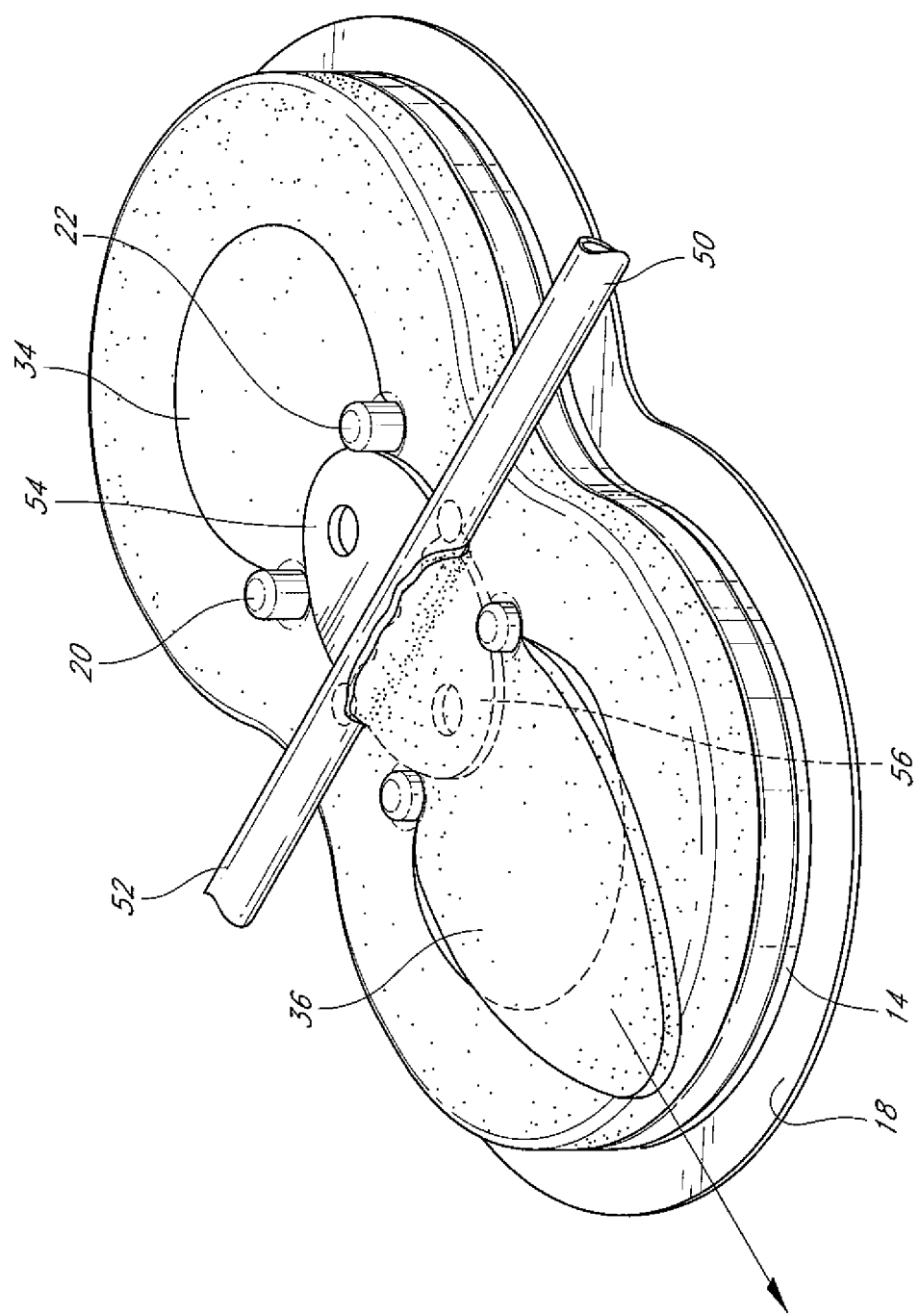
FIG. 8 is a perspective view of the securement device of FIG. 2 with a first wing of the medical article inserted in a cavity or receiving space formed between the anchor pad and the base.

A cavity 38 is formed between at least a portion of the anchor pad 30 and the base 12. In the illustrated embodiment, the cavity 38 is formed at least between the tabs 34, 36 and the base 12. The flexible tabs 34, 36 can be lifted to expose the cavity 38, as seen in FIG. 8. The locating formations 20, 22, 24, 26 extend from the base 12 and into the cavity 38. In the illustrated embodiment, the formations 20, 22, 24, 26 are disposed adjacent to the proximal and distal sides of the tabs 34, 36 and extend in and through the pad 30. An abutment surface on the one or more formations 20, 22, 24, 26 inhibit movement of the medical article in at least one direction. While the formations 20, 22, 24, and 26 are illustrated as extending substantially above the pad 30 in the figures, it is only necessary for them to protrude sufficiently into the cavity 38 so as to interact with the medical article and therefore do not need to extend above the pad 30.

FIG. 3 is top view of the securement device of FIG. 2. In this view, it is evident that the anchor pad 30 and the base 12 of the shown embodiment are of similar shape and size. In other embodiments, the anchor pad 30 and the base 12 are dissimilar in size. For example, the base 12 may be enlarged to provide a larger contact area that provides greater stability and adhesion to the patient's skin, wherein the size of the anchor pad 30 remains of a size commensurate to the size of the medical article being attached. Of course the lower surface of the base 12 may be attached to a third layer or structure. The third layer or structure can include the adhesive surface or layer 14 on its lower surface.

FIG. 4 is a side view of the securement device 10 of FIG. 2. FIG. 5 is a front view of the securement device 10, and FIG. 6 is a cross-sectional view of the securement device 10 through the formations 24, 26. As is most clearly shown in FIG. 3, the anchor pad 30 and the base 12 of the illustrated embodiment are of similar thickness. In other embodiments, the anchor pad 30 and base 12 are of dissimilar thickness. For example, the base 12 may be made thinner to provide the same basic functionality at lower costs. The base 12 may be made thicker to provide additional padding and comfort for the patient. The anchor pad 30 may be formed of a thickness that provides enough strength to resist motion of the medical article without tearing.

As most clearly shown in FIG. 6, the formations 24, 26 extend from the base 12 and entirely through the anchor pad 30 at least when the cavity 38 is not formed between the anchor pad 30 and the base 12. When the cavity 38 is formed, as most clearly illustrated in FIG. 10, the formations 24, 26 extend to a lesser extent through the anchor pad 30 at least in a region over the cavity 38.

As explained above, the formations 24, 26 instead could extend from the anchor pad 30 in a downward direction towards the base 12. The base 12 could further include receptacles on its top surface to receive the distal ends of the formations 24, 26 at least when the cavity 38 is not formed. When the cavity 38 is formed, the distal ends of the formations 24, 26 would extend a shorter distance into the receptacles or not at all. It may be advantageous for at least the distal most portions of the formations 22, 24 to extend into either the anchor pad 30 or the base 12 to improve the stability of the formation 22, 24.

Figure 7:
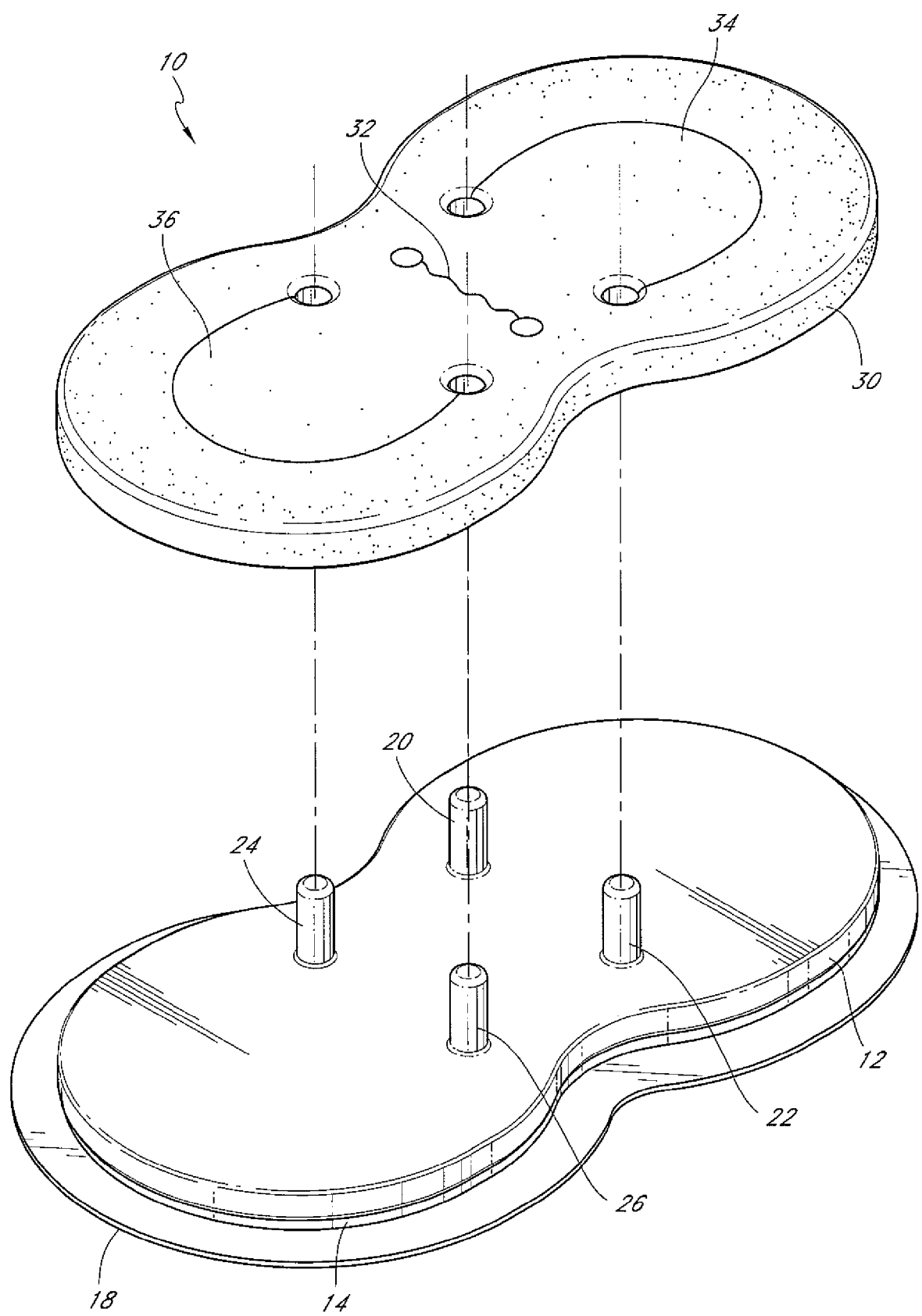
FIG. 7 is an exploded, perspective view of the securement device of FIG. 2 showing the alignment of the base or lower layer and the anchor pad or upper layer.

FIG. 7 is exploded, perspective view of the securement device 10 of FIG. 2 showing the formations 20, 22, 24, and 26 in the base 12 aligned with the openings in the anchor pad 30. While the anchor pad 30 may be manufactured from multiple components, it may be preferred to manufacture the anchor pad 30 from a single layer of material as is illustrated in FIG. 7. The anchor pad 12 has three incisions formed thereon. Two of the incisions define the flexible tabs 34, 36 while the third incision defines the retainer opening 32. In the illustrated embodiment, the incisions forming the flexible tabs 34, 36 have a semi-circular shape. The incision forming the opening 32 has an irregular shape. The incisions may be formed by method known by those skilled in the art including punching or cutting with a blade or a laser.

The anchor pad 30 can have one or more receptacles, holes, or openings. In the illustrated embodiment the anchor pad 30 has four openings for receiving at least portions of the locating formations 20, 22, 24, 26. To assemble the anchor pad 30 to the base 12, the anchor pad 30 is brought in contact with the base 12 with the four openings aligned with the formations 20, 22, 24, 26. As mentioned, the protrusions may not necessarily extend beyond the anchor pad 30.

The base 12 and the anchor pad 30 are secured together so as to create a cavity 38 between the anchor pad 30 and base 12. At least a portion of the cavity 38 is preferably located between the flexible tabs 34, 26 and base 12. Securing at least a portion of the base 12 to the anchor pad 12, or vice versa, may be accomplished via a variety of methods known to those skilled in the art including fusion or adhesive.

FIG. 8 is a perspective view of the securement device 10 of FIG. 2 with one of two wings 56 of the medical article 50 inserted through the retainer opening 32 and into the cavity 38. The securement device 10 is designed for use with a medical article, such as a catheter 50. The catheter 50, in this case, has an elongated body 52 and a mounting portion in the form of wings 54, 56. However, any medical article that has an elongated body and a member that extends in an outward direction away from the body can be retained by the device 10. For example, the member extending from the body can be placed within the cavity 38 while the body is placed in the opening 32. The size and shape of the cavity 38 can be selected based on the shape of the member to be retained.

As seen in the figures, the wings 54, 56 have apertures formed therein, which is common for attachment of sutures in other applications. Of course, if suture openings are desired in the securement device 10 as well, they may be provided.

The catheter 50 is mounted to the securement device 10 by positioning the mounting portion or wings 54, 56 in the cavity 38 and allowing the edges of the retainer opening 32 to close around the tube 52 or line. As the edges of the slit 32 are irregular, they tend to securely grip the portion of the medical device positioned therebetween. The mounting portions 54, 56 are positioned beneath the tabs 34, 36 to hold them in place. Tape or a dressing can be applied over the anchor pad 30, if desired, without disturbing the medical article 50.

The abutment surfaces of the one or more locating formations 20, 22, 24, 26 preferably abut the edges of the mounting portions 54, 56, thereby inhibiting movement of the medical article 50 with respect to the device 10. In some embodiments, an inner wall formed by the anchor pad 30 extends generally normal to the top surface of the base 12 and around at least a portion of the cavity 38 may further inhibit motion of the secured medical article.

Each pair of formations 20, 22, and 24, 26 may at least partially define a portion of a channel, passageway, space, or receiving area configured to receive one of the mounting portions 54, 56. The anchor pad 30 and base 12 prevent rotation of the medical article about the longitudinal axis. The formations 20, 22, 24, and 26 may further prevent rotation of the medical article about the transverse axis.

Figure 9:
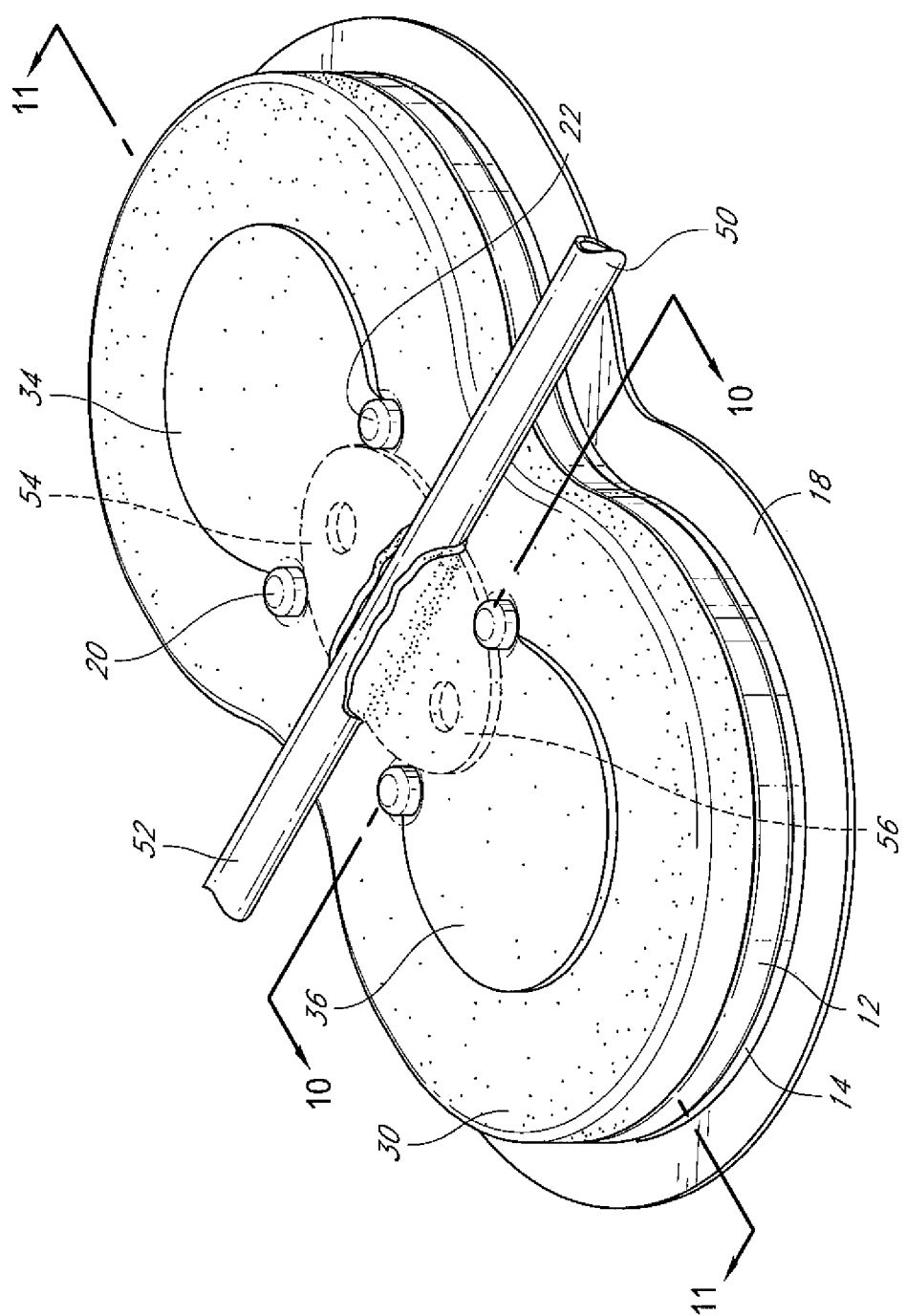
FIG. 9 is a perspective view of the securement device of FIG. 2 with the first and second wings of the medical article inserted into the cavity.

As can be seen in FIG. 9, the wing 54 abuts the formations 20, 22 and the tab 34 covers at least a portion of the wing 54. The wing 56 abuts the formations 24, 26 and the tab 36 covers at least a portion of the wing 56. The locating formations 20, 22, 24, 26 also act as guide surfaces, especially due to the rounded edges, during insertion of the medical article 50 into the cavity by directing the wings 54, 56 into the channel.

In use, the desired location of the medical article 50 and securement device 10 on the patient 1 is determined. The securement device 10 is then secured to the patient's skin by removing the release sheet 18, which may be removed, in one form, in sections, and pressing the adhesive surface 14 onto the patient's skin. Then, as illustrated in FIGS. 8 and 9, the catheter 50, in this case, is mounted on the anchor pad 30 by first lifting and pulling the tab 36 to open the retainer opening 32. The pulling of the tab 36 enlarges the retainer opening 32, allowing the wing 56 to fit into the cavity 38 between the base 12 and the anchor pad 30. The wing 54 is inserted into the cavity 38 and guided into proper position with the locating formations or posts 20, 22. The tab 36 is then released.

Next, the tab 34 is lifted and pulled to allow insertion of the wing 54 into the cavity 38 as is illustrated in FIG. 9. The formations 20, 22 guide the wing 54 into proper position and retain the article 50 in the desired orientation. Releasing the tab 34 allows the slit 32 to close around the line 52 of the catheter 50 and hold it in place, as shown in FIG. 9. As a result, the catheter 50 is securely mounted to the securement device 10. Twisting or rotation of the secured medical article about the transverse axis can be inhibited by the locating formations 20, 22, 24, 26. If desired, tape or a dressing, as is commonly used, can be applied over the sides of the anchor pad 30 or tabs 34, 36 without disturbing the arrangement.

Figure 10:
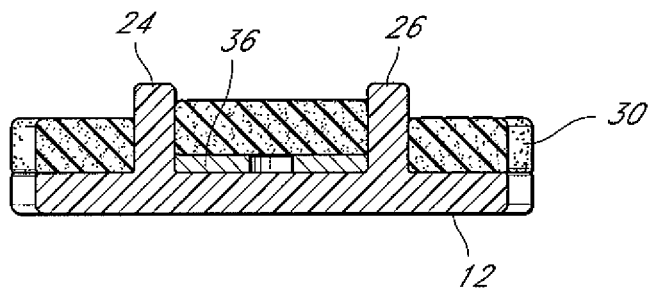
FIG. 10 is a cross-sectional view along lines 10-10 in FIG. 9 and shows one wing of the medical article disposed in the cavity and between two locating formations.
Figure 11:
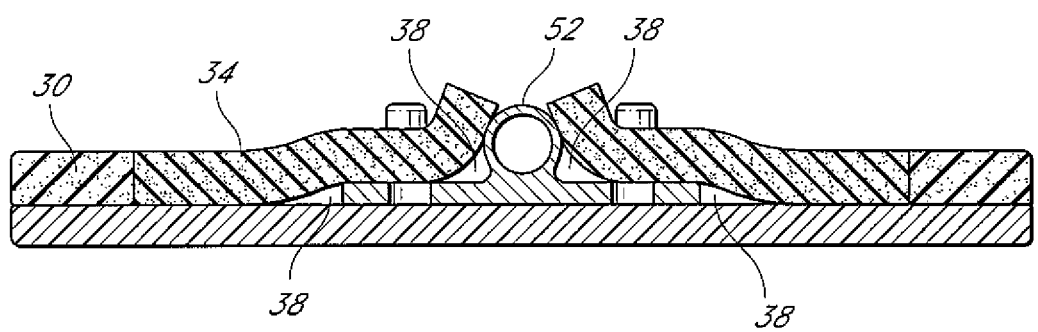
FIG. 11 is a cross-sectional view along lines 11-11 in FIG. 9.

FIGS. 10 and 11 are cross-sectional side and front views, respectively, of the securement device 10 of FIG. 9 with a medical article 50 fully inserted. From these views, one can see the wings 54, 56 of the catheter 50 secured in the cavity 38 formed between the base 12 and the anchor pad 30 with the wings 54, 56 abutted against the locating formations 20, 22, 24, 26. Additionally, in FIG. 11, the elongated body of the medical article 52 of the catheter 50 is secured by the irregular opening 32 of the anchor pad 30.

Figure 12:
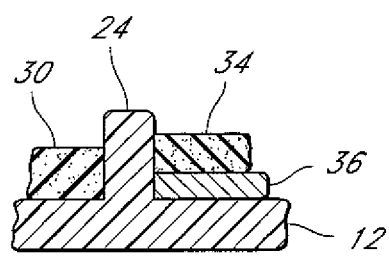
FIG. 12 is an enlarged partial view of FIG. 10 showing the abutment of one wing against one formation.
Figure 13:
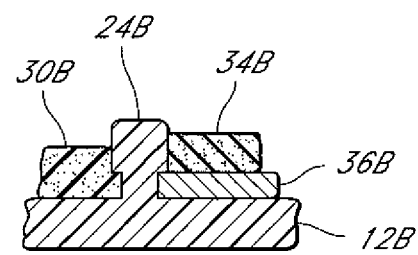
FIG. 13 is an enlarged view similar to FIG. 12 but shows an embodiment of a formation that has an elongated shaft and enlarged head.

FIG. 12 is an enlarged partial view of FIG. 10 showing the abutment of one wing against one formation. The wing 36 is shown resting atop the base 12, abutted against the post 24, and covered by the tab 34. Although one embodiment has been particularly described, other embodiments of the device are envisioned. It is also possible to form the formations with a locking structure, such as a groove or cut-out to hold the mounting portion of the medical article 50 against the base 12. In one embodiment, shown in FIG. 13, the locating formations 24B are formed with an enlarged head that forms a shoulder under which the wing 36B is held. Any type of snap fit arrangement can be used, if desired.

Figure 14A:
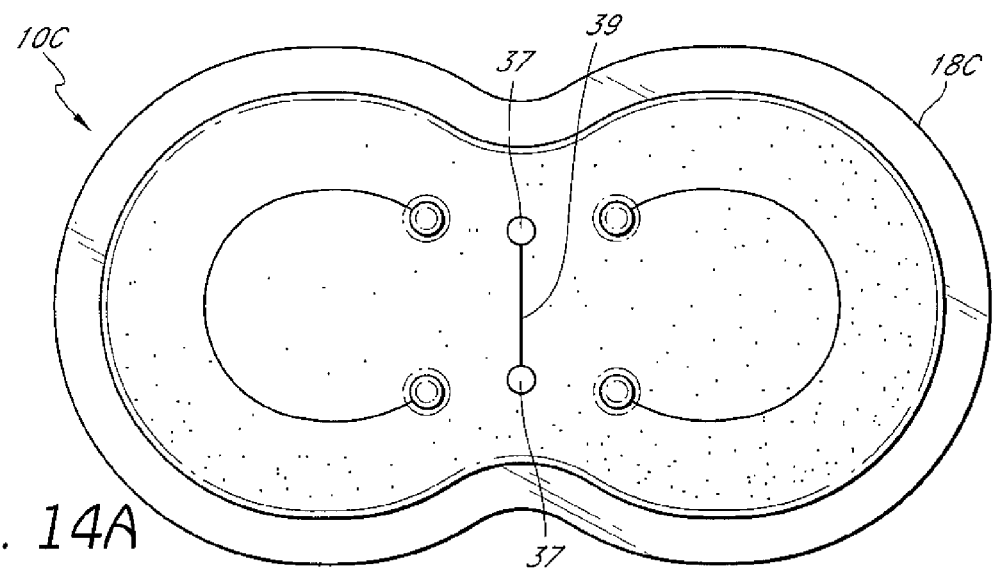
FIGS. 14A-C are top views of additional embodiments of the securement device from FIG. 2 that have different shapes for the retainer opening.
Figure 14B:
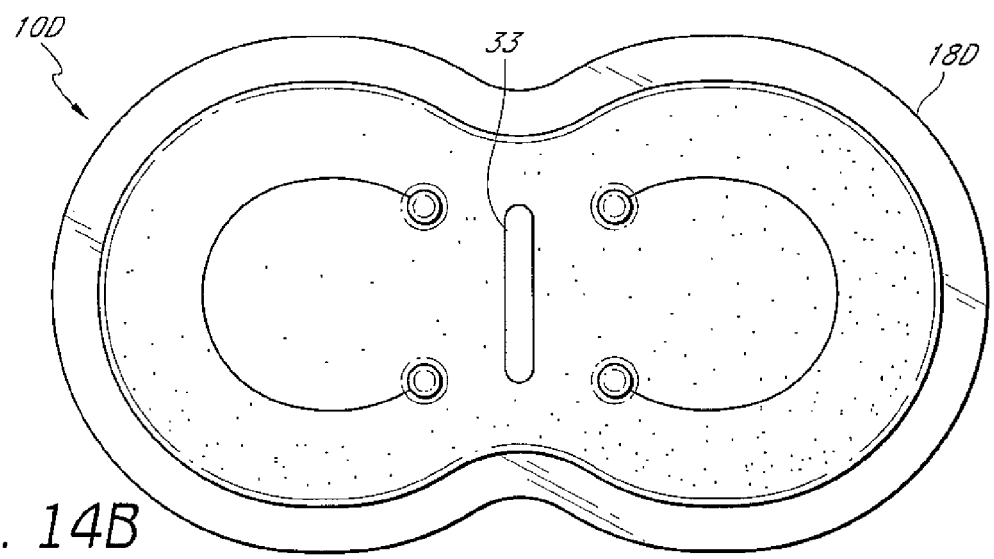
Figure 14C:
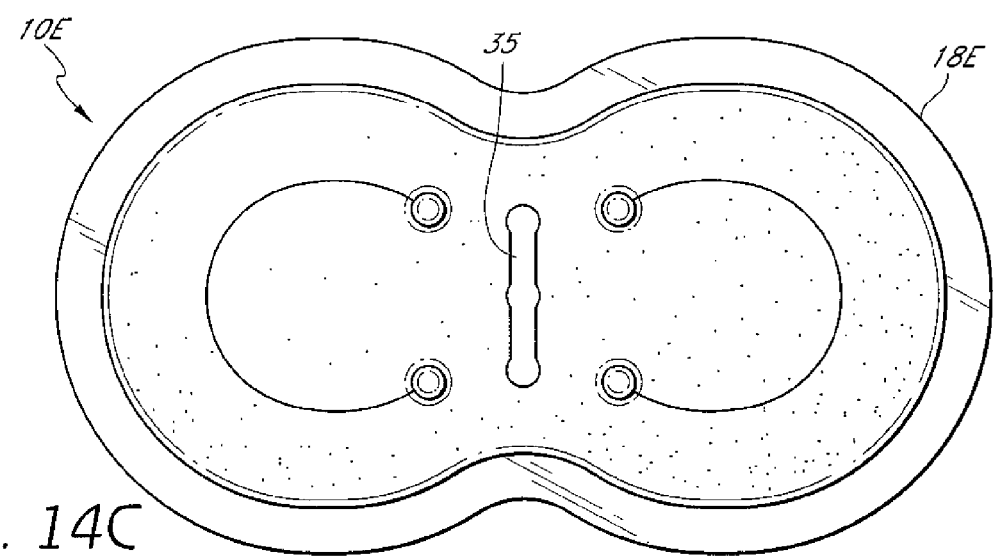

FIGS. 14A-14C are top views of various embodiments of a securement device, each embodiment having a retainer opening of a different shape. In FIG. 14A, the retainer opening 39 of the securement device 10C is formed as a straight slit 39. Forming the retainer opening 39 in this manner may be simpler than forming an irregular opening. Additionally, the slit 39 is accompanied by two holes 37, 38 on either end of the slit 39. The holes prevent the anchor pad from tearing at the ends of the slit 39.

In the embodiment of a securement device 10D shown in FIG. 14B, the retainer opening is a wide slot 33 so that a gap is formed between the sides of the slot 33 even when a medical article is not secured within the device 10D. A wide slot 33 may facilitate placement of the medical article into the cavity 38. The embodiment illustrated in FIG. 14C has an irregular slot 35 that combines the geometry of the two slots 39, 33.

Figure 15:
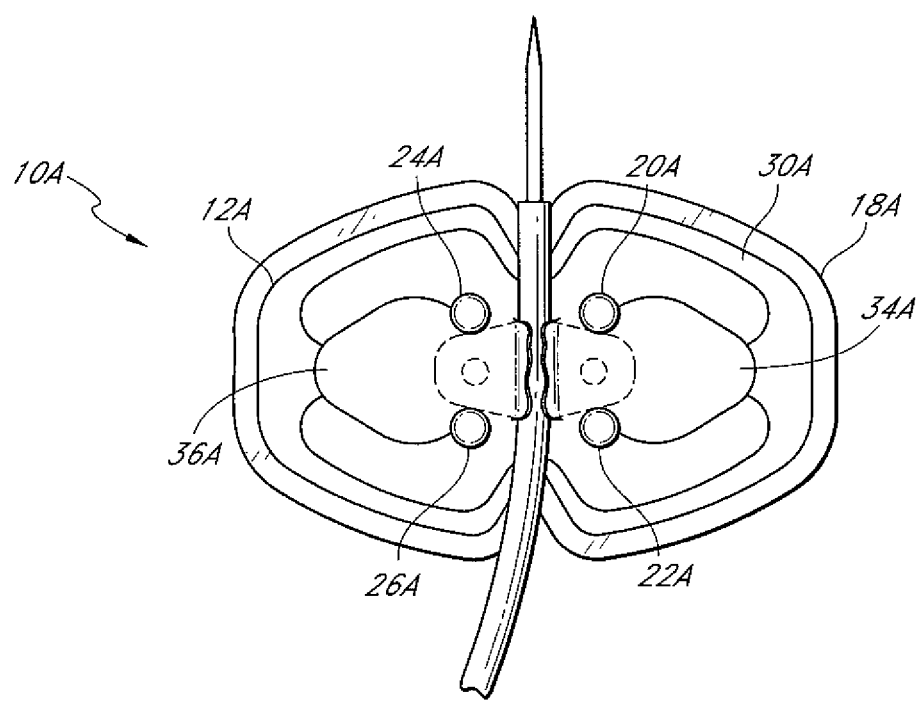
FIG. 15 is a top view of a securement device according to another embodiment of the present invention.

FIG. 15 shows another embodiment of a securement device 10A, in which the lateral ends of the flexible tabs 34A, 36A are not surrounded entirely by the anchor pad 30A. In this embodiment the anchor pad 30A is smaller than the flexible base 12A, such that that flexible base 12A is visible in the top view. Rather that completely surrounding the flexible tabs 34A, 36A, as in embodiments described above, the anchor pad 30A of the securement device 10A illustrated in FIG. 15 is cut or formed such that the lateral ends of the flexible tabs 34A, 36A are exposed. The locating formations 20A, 22A, 24A, and 26A serve to stabilize the medical article inserted into the securement device 10A as described above with respect to other embodiments. One potential advantage of the embodiment illustrated in FIG. 15 is that the flexible tabs 34A, 36A, having their lateral ends exposed, may be more easily grasped by a user of the securement device 10A.

As will be appreciated, the mounting configuration minimizes the possibility of contamination since tape is not necessary and avoids the discomfort and risks associated with sutures. It also has a low profile so that there is no interference with dressings or the actual medical article. The flexible base and anchor pad allow the device to conform to different body contours and still reliably adhere to a patient. The device is easily applied to a patient by health care personnel, requiring no special skills or training. Additionally, the device can accommodate different size catheters and devices, especially since the retainer opening is flexible and expandable.

The securement device described herein reduces the risks of catheter dislodgement and avoids the risks to both medical personnel and to the patient associated with reinsertion and reattachment of medical articles to a patient.

Various modifications may be made as described herein, and many different embodiments of the device and method can be made while remaining within the spirit and scope of the invention as defined in the claims without departing from such spirit and scope. It is intended that all matter contained in the accompanying specification shall be interpreted as illustrative only and not in a limiting sense.

It is to be understood that not necessarily all objects or advantages disclosed herein may be achieved in accordance with any particular embodiment. Thus, for example, those skilled in the art will recognize that embodiments may be carried out in a manner that achieves or optimizes one advantage or group of advantages as taught herein without necessarily achieving other objects or advantages as may be taught or suggested herein. In addition to the variations described herein, other known equivalents for each feature can be incorporated by one of ordinary skill in this art to construct a device and/or system in accordance with principles of this invention.

While the illustrative embodiments have been described with particularity, it will be understood that various other modifications will be apparent to and can be readily made by those skilled in the art without departing from the spirit and scope of the invention. It is also contemplated that various combinations or sub-combinations of the specific features and aspects of the embodiments may be made and still fall within the scope of the invention. Accordingly, it should be understood that various features and aspects of the disclosed embodiments can be combined with or substituted for one another in order to form varying modes of the disclosed invention. Thus, it is intended that the scope of the present invention herein disclosed should not be limited by the particular disclosed embodiments described above, but by a fair reading of the claims that follow.

What is claimed is:

1. A securement device for securing a medical article to a patient, comprising:
    an adhesive layer configured to contact a patient's skin;
    a base having a receiving surface oriented so as to face away from a patient's body;
    an anchor pad supported by the base and defining a cavity at least when the medical article is retained by the securement device, at least a portion of the anchor pad including an opening and a flexible tab, the opening being configured to receive a portion of the medical article, the flexible tab covering at least a portion of the base and being movable so as to expose at least a portion of the receiving surface between the base and the anchor pad, the flexible tab being movable with respect to the base between a first position in which the cavity is at least partially exposed to receive at least a portion of the medical article and a second position in which at least a portion of the anchor pad covers at least a portion of the received medical article; and
    locating protrusions extending at least partially between the base and the anchor pad at least when the flexible tab is in the second position and the received portion of the medical article is disposed within the cavity, the protrusions defining at least in part a mounting position in the cavity for the received portion of the medical article, wherein at least a portion of the anchor pad is movable in a transverse direction along the locating protrusions.

2. The securement device of claim 1, wherein the opening is a slit.

3. The securement device of claim 1, wherein the opening is a slit with irregular edges configured to grip the portion of the medical article.

4. The securement device of claim 1 further comprising another flexible tab so that a pair of tabs is positioned on opposed sides of the opening.

5. The securement device of claim 1, wherein the anchor pad is secured to the base along at least a portion of its perimeter leaving a central portion as the cavity.

6. The securement device of claim 1, wherein the locating protrusions are posts that extend on each side of the flexible tab.

7. The securement device of claim 1, wherein the locating protrusions include four posts defining the mounting position.

8. A securement device for positioning a catheter on a patient, comprising:
    a base having an adhesive bottom surface and a top surface with locating formations protruding therefrom; and
    a flexible anchor pad disposed on the base and defining a cavity at least when the catheter is retained by the securement device, at least a portion of the anchor pad including a flexible tab, the flexible tab being movable so as to expose at least a portion of the top surface between the base and the anchor pad, wherein the anchor pad includes an elongated opening to the cavity, and the locating formations at least partially define the cavity and limit movement of the catheter in at least one direction, wherein at least a portion of the anchor pad is movable in a transverse direction along the locating formations.

9. The securement device of claim 8, wherein the anchor pad has at least two flexible tabs formed therein that covers the cavity and is deformable to provide access to the cavity.

10. The securement device of claim 8, wherein the movement limited in at least one direction is in a rotation direction about a transverse axis.

11. A retainer for securing a medical line having a fitting to the body of a patient, the retainer comprising:
    a lower layer having a receiving surface that at least partially defines a receiving area for receiving a portion of the fitting, an upper layer disposed on the lower layer and at least partially defining the receiving area, and first and second pairs of posts, at least a portion of the upper layer including a flexible tab, the flexible tab being movable so as to expose at least a portion of the receiving surface between the lower layer and the upper layer, the flexible tab being movable between a closed position in which at least a portion of the upper layer extends over at least a portion of the receiving area and an open position in which the receiving area is at least partially open, the first and second pairs of posts extending between the lower layer and the upper layer at least when the upper layer is in the closed position, at least two of the posts of the first and second pairs of posts being disposed on the receiving area and spaced apart so as to receive at least a first portion of the fitting therebetween, and at least two other posts of the first and second pairs of posts being disposed on the receiving area and spaced apart so as to receive at least a second portion of the fitting therebetween, at least a portion of each of the first and second pairs of posts being located at least partially beneath the upper layer when the upper layer is in the closed position, wherein at least the portion of the upper layer is movable in a transverse direction along the first and second pairs of posts.

12. A retainer according to claim 11, wherein the first and second pairs of posts are arranged at the corners of a rectangle.

13. A retainer according to claim 11, wherein the first and second pairs of posts extend in an upward direction from the bottom layer.

14. A retainer according to claim 11, wherein the upper layer is coupled to the lower layer around the receiving area.

15. A retainer according to claim 11, wherein the upper layer includes at least one receptacle for receiving at least a portion of one post of the first and second pairs of posts when the upper layer is in the closed position.

16. A retainer for securing a medical article to the body of a patient, comprising:
a lower layer having a receiving surface that at least partially defines a receiving area for receiving a portion of the medical article, an upper layer disposed on the lower layer and at least partially defining the receiving area, a first post support and a second post support, at least a portion of the upper layer including a flexible tab, the flexible tab being movable so as to expose at least a portion of the receiving surface between the lower layer and the upper layer, the flexible table being movable between a closed position in which at least a portion of the upper layer extends over at least a portion of the receiving area and an open position in which the receiving area is at least partially open, the first and second post supports extending across at least a portion of the receiving area and between the lower layer and the upper layer, the first post support being disposed on a side of the receiving area, the second post support being disposed on the other side of the receiving area and spaced from the first post support so as to receive at least the portion of the medical article therebetween, wherein at least a portion of the upper layer is movable in a transverse direction along the first and second post supports.

17. A retainer according to claim 16, wherein the upper layer comprises a flexible material.

18. A retainer according to claim 16, wherein the open receiving area is sized to receive the portion of the medical article.

19. A retainer according to claim 16, wherein at least one of the first and second post supports extends upward from the lower layer.

20. A retainer according to claim 16, wherein the upper layer includes an opening for receiving at least a portion of one of the first and second post supports.

21. A retainer according to claim 20, wherein the portion of the post support is received by the opening when the upper layer is in the closed position.

22. A retainer according to claim 20, wherein the portion of the post support is received by the opening when the upper layer is in the open position.

23. An anchoring system according to claim 16, wherein at least one of the first and second post supports comprises a shaft and a radial extension, the shaft being configured to abut a vertical surface of the medical article with a lower facing surface of the radial extension abutting against at least a portion of a top surface of the medical article at least when the upper layer is in the closed position.

24. A retainer according to claim 16 further comprising an adhesive layer coupled to the retainer and adapted to adhesively secure the retainer to the body of a patient.

25. A retainer according to claim 24 further comprising a flexible anchor interposed between the retainer and the adhesive layer.

26. A retainer according to claim 16 further comprising a third post support and a fourth post support, each of the third and fourth posts supports extending between the lower layer and the upper layer at least when the upper layer is in the closed position.

27. A retainer according to claim 16, wherein at least a portion of each of the first and second pairs of post extends through the upper layer at least when the upper layer is in the closed position.

28. A retainer according to claim 16, wherein portions of the first post support and the second post support are spaced apart from each other by a minimal distance which substantially matches a width across the portion of the medical article so as to receive said portion of the medical article between the first and second posts supports at the point of minimal distance and inhibit longitudinal movement of the medical article relative to the retainer.

29. A securement device for securing a medical line to a body of a patient, the medical line having a fitting that includes a pair of laterally extending wings, the securement device comprising:
a base layer having a mounting surface at least partially covered by an adhesive for attaching the securement device to the body of the patient, and a receiving surface accessible from an opposite side of the base layer;
a retainer layer disposed on the base layer and including a flexible tab, the flexible tab being movable so as to expose at least a portion of the receiving surface between the base layer and the retainer layer, the retainer layer having a peripheral edge and forming at least one interior wall, the interior wall extending normal to the receiving surface and being disposed within the peripheral edge of the retainer layer, the interior wall and the receiving surface of the base layer together defining at least a portion of a space at least when the fitting is retained by the securement device, the space being configured to receive at least a portion of one of the laterally extending wings of the fitting and being disposed between the base layer and the retainer layer; and
at least one protrusion extending from the base layer adjacent to the space and configured to abut against at least a portion of the received lateral wing, wherein at least a portion of the retainer layer is movable in a transverse direction along the at least one protrusion.

30. A securement device for securing a fitting on a medical line having an elongated body to a body of a patient, the fitting including at least one laterally extending surface that projects beyond the body of the medical line from at least one side of the medical line, the securement device comprising:
a lower layer having a mounting surface at least partially covered by an adhesive layer for attaching the securement device to the patient's body, and a receiving surface oriented so as to face away from the patient's body, the receiving surface including at least two posts spaced apart so as to receive at least a portion of the at least one laterally extending surface of the fitting therebetween;
an upper layer disposed on the lower layer and defining a receiving space at least when the fitting is retained by the securement device, at least a portion of the upper layer including a flexible tab, the flexible tab being movable so as to expose at least a portion of the receiving surface between the lower layer and the upper layer for receiving the laterally extending surface of the fitting, wherein at least the portion of the upper layer is movable in a transverse direction along the at least two posts.

* * * * *